US00PP25562P3

(12) United States Plant Patent
Kapiteijn

(10) Patent No.: US PP25,562 P3
(45) Date of Patent: May 12, 2015

(54) *ZANTEDESCHIA* PLANT NAMED 'CAPTAIN LOVELY'

(50) Latin Name: *Zantedeschia sprengeri*
Varietal Denomination: CAPTAIN LOVELY

(71) Applicant: Antonius Simon Johannes Kapiteijn, Anna Palowna (NL)

(72) Inventor: Antonius Simon Johannes Kapiteijn, Anna Palowna (NL)

(73) Assignee: Kapiteyn Breeding B.V. (NL)

( * ) Notice: Subject to any disclaimer, the term of this patent is extended or adjusted under 35 U.S.C. 154(b) by 110 days.

(21) Appl. No.: 13/987,390

(22) Filed: Jul. 19, 2013

(65) Prior Publication Data

US 2015/0026857 P1 Jan. 22, 2015

(30) Foreign Application Priority Data

Jul. 23, 2012 (QZ) ..... 20121628

(51) Int. Cl.
*A01H 5/00* (2006.01)

(52) U.S. Cl.
USPC ..... Plt./490

(58) Field of Classification Search
USPC ..... Plt./490
See application file for complete search history.

*Primary Examiner* — Kent L Bell
(74) *Attorney, Agent, or Firm* — Cassandra Bright

(57) ABSTRACT

A new and distinct *Zantedeschia* cultivar named 'CAPTAIN LOVELY' is disclosed, characterized by red-puprle spathe color, distinctive yellow spadix, and green foliage infrequently spotted or striped with white. The new variety is commercially suitable for indoor plant production.

1 Drawing Sheet

Latin name of the genus and species: *Zantedeschia sprengeri.*

Variety denomination: 'CAPTAIN LOVELY'.

BACKGROUND OF THE INVENTION

This application claims priority benefit to European Union Plant Breeder's Rights application number 2012/1628 filed Jul. 23, 2012. The new cultivar is a product of a planned breeding program. The new variety originated from a cross pollination, made by the inventor in 2007, of a proprietary seed parent identified as '04335' and a proprietary pollen parent identified as '03.4402sc.59', both *Zantedeschia sprengeri.*

The new variety was discovered and selected by the inventor, Anthonius Simon Johannes Kapiteijn, a citizen of the Netherlands, in 2009 in a group of seedlings resulting from the crossing. The new cultivar was found in a commercial greenhouse belonging to the inventor in Anna Paulowna, the Netherlands.

Asexual reproduction of the new cultivar 'CAPTAIN LOVELY' was first performed by micropropagation at a commercial laboratory in the Netherlands during 2010. Micropropagated plants were subsequently grown out to produce tubers. 'CAPTAIN LOVELY' has been reproduced by both micropropagation and tubers and has shown that the unique features of this cultivar are stable and reproduced true to type.

SUMMARY OF THE INVENTION

The cultivar 'CAPTAIN LOVELY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAPTAIN LOVELY.' These characteristics in combination distinguish 'CAPTAIN LOVELY' as a new and distinct *Zantedeschia* cultivar:

1. Red-purple spathe color.
2. Distinctive yellow spadix
3. Green foliage with infrequent white spots and stripes.

PARENT COMPARISON

Plants of the new cultivar 'CAPTAIN LOVELY' are similar to plants of the seed parent variety, in most horticultural characteristics, however, plants of the new cultivar produce darker colored spathes than the seed parent.

Plants of the new cultivar 'CAPTAIN LOVELY' are similar to plants of the pollen parent variety, in most horticultural characteristics, however, plants of the new cultivar produce spathes with less purple color than the pollen parent.

COMMERCIAL COMPARISON

Plants of the new cultivar 'CAPTAIN LOVELY' are similar to plants of the unpatented variety, *Zantedeschia sprengeri* 'Captain Roxy', in most horticultural characteristics. Plants of the new variety, however, have whites spots of the foliage not found on 'Captain Roxy'. Additionally, plants of 'Captain Lovely' are shorter and produce larger inflorescences with a more intense coloration. Tubers of the new variety produce more shoots, and therefore more inflorescences per plant than 'Captain Roxy'.

BRIEF DESCRIPTION OF THE PHOTOGRAPH

The accompanying photograph in FIG. 1 illustrates in full color a typical plant of 'CAPTAIN LOVELY' grown in a greenhouse in Anna Paulowna, the Netherlands. The plant is approximately 2 years old, shown growing in 14 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CAPTAIN LOVELY' plants grown in a climate controlled greenhouse in Anna Paulowna, the Netherlands. Temperatures ranged from 18° C. to 22° C. day to 12° C. to 16° C. at night. No artificial light or photoperiodic treatments were given to the plants. The following chemical treatments were used; GA 3 growth regulator at an unspecified amount during production. Before planting growth retardant, padobutrazol at a dose of 1 ppm was given. Measurements and numerical values represent averages of typical plant types.

Botanical classification: *Zantedeschia sprengeri* cultivar 'CAPTAIN LOVELY'.

PROPAGATION

Time to initiate roots: Approximately 10 days from tissue culture plantlet at approximately 18 to 22° C.

Time to produce rooted plantlet: Approximately 10-30 days at approximately to 18-22° C.

Typical propagation material: Plants for commercial flowering potted plant production are typically produced by planting a 2 year old tuber.

Root description: Moderately dense, moderately branched, slightly fibrous, non-fleshy colored white; near RHS NN155C.

PLANT

Plant shape: Broad obovate.

Height: Approximately 31.5 cm to top of highest leaf. Approximately 22.6 cm to top of highest inflorescence.

Plant spread: Average: 33.8 cm.

Typical pot size: 14 cm circular pots and larger.

Growth rate: Moderate.

Branching characteristics: No branching. Leaves emerge direct from base of plant.

Number of clumps of leaves per plant of this age: Average: 8.

Number of leaves per clump: Approximately 4.

Number of leaves per plant: Approximately 32.

Age of plant described: Approximately 24 months from a tuber.

FOLIAGE

Arrangement: Equitant.

*Average length(excluding petiole)*.—Approximately 15.5 cm.

*Average width*.—Approximately 7.1 cm.

*Shape of blade*.—Ovate.

*Aspect*.—Leaves in an average angle of 60° (varying between 30° and 90°) to horizontal (=0°).

*Apex*.—Mucronate.

*Base*.—Attenuate to obtuse.

*Margin*.—Entire, undulate.

*Texture of top surface*.—Glabrous, matte.

*Texture of bottom surface*.—Glabrous, very slightly glossy.

*Color*.—Young foliage upper side: Near RHS Green137B and 143A, slightly striped irregularly transparent green-white; near RHS 157C and 157D. Young foliage under side: Near RHS Green 137C, slightly striped irregularly transparent green-white; near RHS 157C and 157D. Mature foliage upper side: Near RHS Green 137B, slightly striped irregularly transparent white; near RHS 155C. Mature foliage under side: Near RHS Green RHS 137C and 138A, slightly striped irregularly transparent white; near RHS 155C.

Venation:

*Type*.—Pinnate.

*Venation coloration upper side*.—Green; near RHS 143C.

*Venation coloration under side*.—Green; near RHS 143C.

Petiole:

*Length*.—Approximately 13.6 cm.

*Width*.—Approximate width at distal end of petiole: 0.6 cm, at proximal end, approximately 0.8 cm.

*Color*.—Yellow-green; near RHS 144B.

*Strength*.—Moderate.

Wing:

*Length*.—Approximately 5.2 cm.

*Width*.—Approximately 0.5 cm.

*Color*.—Yellow-green; near RHS 145C and 145D.

INFLORESCENCE

Arrangement: Individual inflorescences grow from the center of each clump.

Flowering habit: Once a year, from late spring into summer.

Quantity of spathes per plant: On average: 12 fully open spathes in good condition.

Natural flowering season: Late spring into summer.

Fragrance: No fragrance.

Self-cleaning or persistent: Persistent.

Flower longevity: Flowers stay in good condition approximately 3-4 weeks on the plant.

Spathe:

*Aspect*.—Upright, straight on top of peduncle. Overall semi spiral, with backward curve at top of spathe.

*Length*.—Approximately 8.6 cm.

*Width*.—Approximately 5.5 cm.

*Shape*.—Broad ovate, base folded around spadix.

*Margin*.—Entire, revolute, slightly undulate.

*Apex*.—Mucronate.

*Base*.—Broad cuneate, circular (folded around spadix).

*Apperance*.—Shiny.

*Color*.—Front when opening: Red-purple to greyed-purple; in between near RHS 59A and N186D. Back when opening. Red-purple to greyed-red; in between near RHS 64A and 186A. Front when mature: Red-purple to greyed-purple; in between near RHS 59A and N186D. Back when mature: Red-purple to greyed-red; in between near RHS 64A and 186A. Fading to: Not fading.

Spadix:

*Shape*.—Columnar.

*Tip*.—Obtuse.

*Base*.—Obtuse.

*Length*.—Approximately 2.7 cm.

*Width*.—Approximately 0.8 cm.

*Color*.—When opening: Lower 40% (female flowers) white; near RHS 155A, upper 60% (male flowers) yellow-orange; near RHS 15A and 15B. Mature: Near RHS Lower 40% (female flowers) yellow-green; near RHS 154D, tinged purple; near RHS N77B, upper 60% (male flowers) yellow-orange; near RHS 15A and 15B.

*Quantity of flowers per spadix*.—Approximately 36 female flowers (consisting of a single style and ovary) approximately 300 male flowers (consisting of anthers only).

*Spadix flower arrangement*.—Female flowers (consisting of a single style and ovary) arranged at the base of the spadix (lower 40%), male flowers (consisting of anthers only) arranged above the female flowers (upper 60% of the spadix).

*Spadix flower diameter*.—Female flowers (consisting of a single style and ovary) Approximately 0.25 cm, male flowers (consisting of anthers only) approximately 0.1 cm.

*Spadix flower depth*.—Female flowers (consisting of a single style and ovary) Approximately 0.2 cm, male flowers (consisting of anthers only) approximately 0.75 cm.

Scape:

*Length*.—Approximately 15.6 cm.

*Width*.—Approximately 0.6 cm.

*Color*.—Yellow-green; near RHS 144B.

*Strength*.—Moderate.

REPRODUCTIVE ORGANS

Minute organs, of immeasurable size, and the following coloration:

*Style and ovary of female flowers*.—Yellow-green; near RHS 154D, tinged purple; RHS N77B. Stigma colored yellow-orange; near RHS 15A.

*Visible male flower parts*.—Anthers colored yellow-orange; near RHS 15A and 15B, pollen colored yellow; near RHS 11D.

OTHER CHARACTERISTICS

Disease/pest resistance: Neither resistance nor susceptibility to diseases or pests has been observed in this variety.

Drought tolerance and temperature tolerance: The new cultivar is a typical *Zantedeschia*, tolerant of temperatures approximately 10° C. to 28° C. and does not tolerate drought.

Fruit/seed production: Not observed.

What is claimed is:

1. A new and distinct cultivar of *Zantedeschia* plant named 'CAPTAIN LOVELY' as herein illustrated and described.

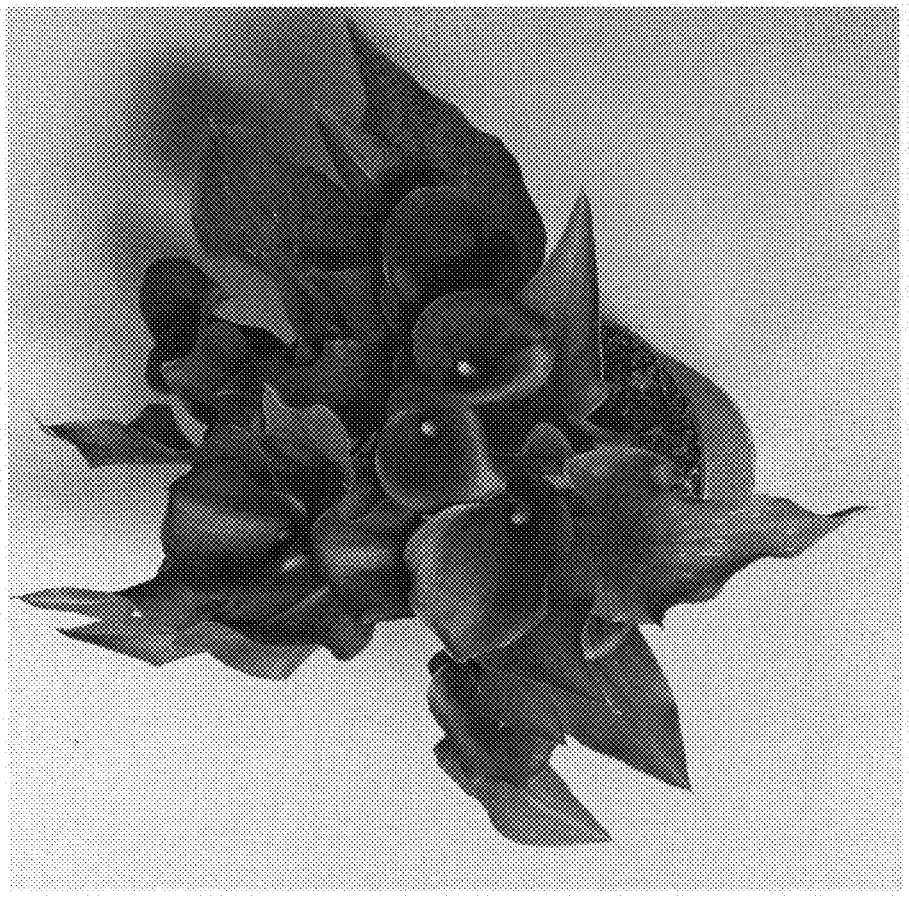

* * * * *